US006632434B2

(12) United States Patent
Haake

(10) Patent No.: US 6,632,434 B2
(45) Date of Patent: Oct. 14, 2003

(54) LEPTOSPIRAL MAJOR OUTER MEMBRANE PROTEIN, LIPL 32

(75) Inventor: David A. Haake, Culver City, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/925,118

(22) Filed: Aug. 8, 2001

(65) Prior Publication Data

US 2002/0127239 A1 Sep. 12, 2002

Related U.S. Application Data

(62) Division of application No. 09/028,586, filed on Feb. 24, 1998, now Pat. No. 6,306,623.

(51) Int. Cl.⁷ .................. A61K 39/00; A61K 39/02; A61K 39/38; C07K 1/00; C07K 14/00
(52) U.S. Cl. ................. 424/184.1; 424/185.1; 424/190.1; 424/234.1; 424/262.1; 530/350
(58) Field of Search .......................... 424/184.1, 185.1, 424/190.1, 234.1, 262.1; 530/350

(56) References Cited

U.S. PATENT DOCUMENTS

| 5,178,859 A |   | 1/1993 | Simon et al. |
| 5,837,263 A | * | 11/1998 | Haake |

FOREIGN PATENT DOCUMENTS

| WO | WO 95/32220 | 11/1995 |

OTHER PUBLICATIONS

Plotkin (*Vaccines* W.B. Sanders Co. Philadelphia, p. 571) 1988.*
Leite et al (Revista da Sociedade Brasileria de Medicina Tropical vol. 29(5) pp 483–489) 1996.*
Agunloye (Trop. Vet. vol. 14 pp. 17–21) 1996.*
Kim, M.J., "Leptospira Interrogans Serovar Lai Hemolysis–Associated Protein–1 (hap–1) and Hemolytic Protein (sphH) Genes," GenBank, Sep. 3, 1997, EMBL Database (XP–002111261), 9 pages.

* cited by examiner

*Primary Examiner*—Mark Navarro
(74) *Attorney, Agent, or Firm*—Gray Cary Ware & Freidenrich, LLP

(57) ABSTRACT

An antigenic preparation is provided containing an outer membrane protein associated with pathogenic strains of Leptospira. The protein has been designated ALipL32" for Alipoprotein from Leptospira≡ and because the isolated polypeptide migrates to a position corresponding to a molecular weight of 32 kD in a denaturing polyacrylamide gel. The invention provides polynucleotides encoding LipL32 and antibodies that bind the protein which are useful in the diagnosis of leptospirosis. In addition, LipL32 can be used immunologically as a vaccine for spirochete-associated pathologies.

8 Claims, 1 Drawing Sheet

FIGURE 1

```
ATG AAA AAA CTT TCG ATT TTG GCT ATC TCC GTT GCA CTC TTT GCA AGC
Met Lys Lys Leu Ser Ile Leu Ala Ile Ser Val Ala Leu Phe Ala Ser

ATT ACC GCT TGT GGT GCT TTC GGT GGT CTG CCA AGC CTA AAA AGC TCT
Ile Thr Ala Cys Gly Ala Phe Gly Gly Leu Pro Ser Leu Lys Ser Ser

TTT GTT CTG AGC GAG GAC ACA ATC CCA GGG ACA AAC GAA ACC GTA AAA
Phe Val Leu Ser Glu Asp Thr Ile Pro Gly Thr Asn Glu Thr Val Lys

ACG TTA CTT CCC TAC GGA TCT GTG ATC AAC TAT TAC GGA TAC GTA AAG
Thr Leu Leu Pro Tyr Gly Ser Val Ile Asn Tyr Tyr Gly Tyr Val Lys

CCA GGA CAA GCG CCG GAC GGT TTA GTC GAT GGA AAC AAA AAA GCA TAC
Pro Gly Gln Ala Pro Asp Gly Leu Val Asp Gly Asn Lys Lys Ala Tyr

TAT CTC TAT GTT TGG ATT CCT GCC GTA ATC GCT GAA ATG GGA GTT CGT
Tyr Leu Tyr Val Trp Ile Pro Ala Val Ile Ala Glu Met Gly Val Arg

ATG ATT TCC CCA ACA GGC GAA ATC GGT GAA CCA GGC GAT GGA GAC TTA
Met Ile Ser Pro Thr Gly Glu Ile Gly Glu Pro Gly Asp Gly Asp Leu

GTA AGC GAC GCT TTC AAA GCG GCT ACC CCA GAA GAA AAA TCA ATG CCA
Val Ser Asp Ala Phe Lys Ala Ala Thr Pro Glu Glu Lys Ser Met Pro

CAT TGG TTT GAT ACT TGG ATC CGT GTA GAA AGA ATG TCG GCG ATT ATG
His Trp Phe Asp Thr Trp Ile Arg Val Glu Arg Met Ser Ala Ile Met

CCT GAC CAA ATC GCC AAA GCT GCG AAA GCA AAA CCC GTT CAA AAA TTG
Pro Asp Gln Ile Ala Lys Ala Ala Lys Ala Lys Pro Val Gln Lys Leu

GAC GAT GAT GAT GAT GGT GAC GAT ACT TAT AAA GAA GAG AGA CAC AAT
Asp Asp Asp Asp Asp Gly Asp Asp Thr Tyr Lys Glu Glu Arg His Asn

AAG TAC AAC TCT CTT ACT AGA ATC AAG ATC CCT AAT CCT CCA AAA TCT
Lys Tyr Asn Ser Leu Thr Arg Ile Lys Ile Pro Asn Pro Pro Lys Ser

TTT GAC GAC CTG AAA AAC ATC GAT ACT AAA AAA CTT TTA GTA AGA GGT
Phe Asp Asp Leu Lys Asn Ile Asp Thr Lys Lys Leu Leu Val Arg Gly

CTT TAC AGA ATT TCT TTC CCT ACC TAC AAA CCA GGT GAA GTG AAA GGA
Leu Tyr Arg Ile Ser Phe Pro Thr Tyr Lys Pro Gly Glu Val Lys Gly

TCT TTC GTT GCA TCT GTT GGT CTG CTT TTC CCA CCA GGT ATT CCA GGT
Ser Phe Val Ala Ser Val Gly Leu Leu Phe Pro Pro Gly Ile Pro Gly

GTG AGC CCG CTG ATC CAC TCA AAT CCT GAA GAA TTG CAA AAA CAA GCT
Val Ser Pro Leu Ile His Ser Asn Pro Glu Glu Leu Gln Lys Gln Ala

ATC GCT GCT GAA GAG TCT TTG AAA AAA GCT GCT TCT GAC GCG ACT AAG
Ile Ala Ala Glu Glu Ser Leu Lys Lys Ala Ala Ser Asp Ala Thr Lys

TAA     (SEQ ID NO:1)
stop    (SEQ ID NO:2)
```

Nucleotide sequence (SEQ ID NO:1) and deduced amino acid sequence(SEQ ID NO:2) of lipL32. The location of the TAA stop codon is indicated.

LEPTOSPIRAL MAJOR OUTER MEMBRANE PROTEIN, LIPL 32

The present application is a divisional of U.S. application Ser. No. 09/028,586 and filed on Feb. 24, 1998 now U.S. Pat. No. 6,306,623.

TECHNICAL FIELD

This invention relates generally to antigenic preparations and more specifically to a Leptospira outer membrane protein (LipL32) which is useful for inducing a protective immune response in a subject.

BACKGROUND

Spirochetes are helically shaped, motile bacteria. Among the spirochetes, three genera are identified as pathogens, Treponema, Borrelia and Leptospira. The treponemes include *Treponema pallidum*, the causative agent of the venereal disease syphilis in humans. Other treponemes such as *T. denticola* and *T. vincentii* are usually found in the mouth and have been linked to periodontal disease. Several other spirochetes can cause animal as well as human disease. *Borrelia recurrentis*, which is carried by ticks, causes relapsing fever in which the infected subject suffers repeated bouts of fever and chills. *B. burgdorferi*, also tick-borne, is responsible for Lyme disease, a debilitating ailment known to cause arthritis, loss of myelin from nerve cells and myocarditis. Pathogenic strains of Leptospira frequently cause the zoonotic disease, leptospirosis, and are capable of infecting most mammalian species. At present, there are six pathogenic species and three nonpathogenic species within the genus Leptospira. Infection occurs either through direct contact with an infected animal or indirect contact with contaminated soil or water. In livestock, the disease causes economic losses due to abortion, stillbirth, infertility, decreased milk production, and death.

Efforts to control leptospirosis have been hampered because virulent leptospires have the capacity for both long-term survival in the environment as well as persistent infection and shedding by wildlife and livestock. Currently available leptospiral vaccines produce short-term immunity and do not provide cross-protection against many of the 170 serovars of pathogenic Leptospira (Thiermann, et al., *J.Am. .Vet.Med.Assoc.* 184:722, 1984). These vaccines consist of inactivated whole organisms or outer envelope preparations which produce seroreactivity as determined by microscopic agglutination of intact organisms. The nature of the protective immunogens in these vaccine preparations has not been conclusively elucidated, although several lines of evidence suggest that lipopolysaccharide may confer a degree of serovar-specific protection.

The pathogenesis of leptospirosis is similar to that of other spirochetal diseases, including syphilis (caused by *Treponema pallidum*) and Lyme borreliosis (caused by *Borrelia burgdorferi*). Both syphilis and Lyme borreliosis are characterized by widespread dissemination early in the course of disease, including invasion of the central nervous system. Leptospira share this ability with other pathogenic spirochetes such that meningitis is a common manifestation of leptospirosis. Another feature of spirochetal infections is the ability to persist chronically in the host, as manifested in cases of tertiary syphilis and chronic Lyme arthritis.

Attempts to identify leptospiral outer membrane proteins (OMPs), have led to limited success due to such problems as: 1) the techniques used to identify surface-exposed proteins probably involved damage to the fragile leptospiral outer membrane resulting in exposure of subsurface structures; 2) putative surface-exposed proteins that were identified included a 35–36 kD doublet corresponding to Leptospira endoflagella (Kelson, et al., *J. Med. Microbiol.* 26:47, 1988), which are subsurface structures in spirochetes; and 3) use of sodium docecyl sulfate (SDS) which nonselectively solubilizes proteins irrespective of their native cellular location.

Nunes-Edwards, et al. (*Infect. Immun.* 48:492, 1985) introduced the use of radioimmunoprecipitation and cell fractionation schemes based on the use of SDS in an effort to identify leptospiral OMPs. The leptospires used in their radioimmunoprecipitation procedure were subjected to high speed centrifugation (20,000× g) prior to the addition of antibody. Such high centrifugal forces cause mechanical disruption of the leptospiral outer membrane. Niikura, et al. (*Zbl. Bakt. Hyg. A.* 266:453, 1987) immunoprecipitated SDS-solubilized extracts of virulent and avirulent strains of *L. interrogans* serovar copenhageni that had been labeled by lactoperoxidase-catalyzed surface radioiodination. Since both of these studies precipitated a 35–36 kD doublet consistent with leptospiral endoflagella, there was a concern as to whether the other proteins identified might also have a subsurface rather than a surface location.

Jost, et al. (*J. Med. Microbiol.* 27:143) characterized a monoclonal antibody with specificity for a 35 kD proteinase K sensitive antigen which was present in a leptospiral outer envelope preparation. However, to demonstrate binding of the monoclonal antibody by immunoelectron microscopy, the leptospiral outer membrane had to be disrupted. Doherty, et al. (*J. Med. Microbiol.* 28:143) cloned two leptospiral proteins represented in an SDS-generated outer membrane preparation of *L. interrogans*, but did not provide corroborating evidence that these proteins are either constituents of the outer membrane or are surface-exposed.

Unsuccessful research on the identification of Leptospira and *T. pallidum* OMPs has shown the importance of taking into account spirochetal outer membrane fragility and the lack of outer membrane selectivity of ionic detergents such as SDS (Cunningham, et al., *J.Bacteriol.* 170:5789, 1988; Penn, et al., *J. Gen. Microbiol.* 131:2349, 1985; Stamm, et al., *Infect. Immun.* 55:2255, 1987). Outer membrane proteins are of great importance because they play a key role in bacterial pathogenesis. The identification of outer membrane proteins involved in Leptospira pathogenesis is significant to understanding not only leptospiral outer membrane proteins and their involvement in pathogenesis, but also to understanding other spirochetal outer membrane proteins and their role in pathogenesis.

SUMMARY OF THE INVENTION

The present invention is based on the identification of a leptospiral outer membrane protein which is associated with pathogenic strains of Leptospira. The invention describes an approximately 27.6 kD outer membrane protein, and the gene encoding the protein, originally derived from *L. kirschneri*. The molecular weight was calculated from the deduced amino acid sequence of the polypeptide. The amino acid sequence encodes a membrane lipoprotein with a nineteen amino acid leader peptide, a lipoprotein signal peptidase cleavage site and an amino terminal cysteine. The 27.6 kD protein has been designated ALipL32" for Alipoprotein from Leptospira= and because the isolated polypeptide migrates, in a denaturing polyacrylamide gel, to a position corresponding to a molecular weight of 32 kD. This immunogenic polypeptide is useful for inducing an immune response to pathogenic spirochetal organisms as well as providing a diagnostic target for spirochetal-associated pathologies.

In a first embodiment, the invention provides a substantially purified LipL32 polypeptide and nucleic acid encoding the LipL32 polypeptide. In accordance with another aspect of the invention, an expression vector containing LipL32 nucleic acid is provided. Also included is a method for producing the LipL32 polypeptide.

The invention further provides a pharmaceutical composition useful for inducing an immune response to a pathogenic spirochete in a subject containing an immunologically effective amount of LipL32 in a pharmaceutically acceptable carrier.

In another aspect, the invention provides a pharmaceutical composition useful for providing immunity to a pathogenic spirochete in a subject comprising an immunogenically effective amount of antibody which binds LipL32 in a pharmaceutically acceptable carrier.

In yet another aspect, the invention provides a method for identifying a compound which binds to LipL32 polypeptide that includes incubating components comprising the compound and LipL32 polypeptide under conditions sufficient to allow the components to interact and measuring the binding of the compound to LipL32 polypeptide.

The invention further provides a method of detecting pathogenic spirochete in a sample which includes contacting a sample suspected of containing a pathogenic spirochete with a reagent that binds to the spirochete-specific cell component and detecting binding of the reagent to the component. In one aspect, the reagent that binds to the spirochete-specific cell component is an oligonucleotide probe for the identification of LipL32 nucleic acid. In another aspect, the reagent that binds to the spirochete-specific cell component is an antibody.

In another aspect, the invention provides a method for detecting antibody to LipL32 polypeptide in a sample including contacting the sample with LipL32 polypeptide, or fragments thereof, under conditions which allow the antibody to bind to LipL32 polypeptide and detecting the binding of the antibody to the LipL32 polypeptide.

In yet another aspect, the invention provides a kit useful for the detection of LipL32 polypeptide, nucleic acid encoding LipL32 and antibodies that bind to LipL32.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

FIG. 1 shows a nucleic acid sequence for the lipL32 gene (SEQ ID NO:1) and the deduced amino acid sequence of the LipL32 polypeptide (SEQ ID NO:2).

DETAILED DESCRIPTION OF THE INVENTION

The present invention originated from studies on leptospiral outer membrane proteins. The invention provides an immunogenic polypeptide originally isolated from an outer membrane protein of a pathogenic Leptospira species. Also included is a nucleic acid sequence which encodes the polypeptide. The outer membrane protein is an approximately 27.6 kD protein isolated from *Leptospira kirschneri* which has been termed ALipL32" and is a pathogen-associated exported protein of Leptospira. This immunogenic polypeptide is useful in a pharmaceutical composition for inducing an immune response to pathogenic spirochetes.

LipL32 Nucleic Acid, Polypeptides, Host Cells and Vectors

In a preferred embodiment, the invention provides an isolated polynucleotide sequence encoding a LipL32 polypeptide. An exemplary LipL32 polypeptide of the invention has an amino acid sequence as set forth in SEQ ID NO:2. The term Aisolated≈ as used herein includes polynucleotides substantially free of other nucleic acids, proteins, lipids, carbohydrates or other materials with which it is naturally associated. Polynucleotide sequences of the invention include DNA, cDNA and RNA sequences which encode LipL32. It is understood that all polynucleotides encoding all or a portion of LipL32 are also included herein, as long as they encode a polypeptide with LipL32 activity (e.g., provide an antigenic determinant for Leptospira or other pathogenic spirochetes). Such polynucleotides include naturally occurring, synthetic, and intentionally manipulated polynucleotides. For example, LipL32 polynucleotide may be subjected to site-directed mutagenesis. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of LipL32 polypeptide encoded by the nucleotide sequence is functionally unchanged. Also included are nucleotide sequences which encode LipL32 polypeptide, such as SEQ ID NO:1. In addition, the invention also includes a polynucleotide encoding a polypeptide having the biological activity of an amino acid sequence of SEQ ID NO:2 and having at least one epitope for an antibody immunoreactive with LipL32 polypeptide. Assays provided herein which show association between leptospiral infection and expression of LipL32 can be used to detect the presence LipL32.

The invention includes polypeptides having substantially the same amino acid sequence as set forth in SEQ ID NO:2 or functional fragments thereof, or amino acid sequences that are substantially identical to SEQ ID NO:2. By Asubstantially the same≈ or Asubstantially identical≈ is meant a polypeptide or nucleic acid exhibiting at least 80%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

By Asubstantially identical≈ is also meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein assayed, (e.g., as described herein). Preferably, such a sequence is at least 85%, more preferably identical at the amino acid level to SEQ ID NO:2.

Homology is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications.

By a Asubstantially pure polypeptide≅ is meant an LipL32 polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, LipL32 polypeptide. A substantially pure LipL32 polypeptide may be obtained, for example, by extraction from a natural source (e.g., a plant cell); by expression of a recombinant nucleic acid encoding an LipL32 polypeptide; or by chemically synthesizing the protein. Purity can be measured by any appropriate method, e.g., those described in column chromatography, polyacrylamide gel electrophoresis, or by HPLC analysis.

LipL32 polypeptides of the present invention include peptides, or full length protein, that contains substitutions, deletions, or insertions into the protein backbone, that would still leave a 70% homology to the original protein over the corresponding portion. A yet greater degree of departure from homology is allowed if like-amino acids, i.e. conservative amino acid substitutions, do not count as a change in the sequence. Examples of conservative substitutions involve amino acids that have the same or similar properties. Illustrative amino acid conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine.

Modifications and substitutions are not limited to replacement of amino acids. For a variety of purposes, such as increased stability, solubility, or configuration concerns, one skilled in the art will recognize the need to introduce, (by deletion, replacement, or addition) other modifications. Examples of such other modifications include incorporation of rare amino acids, dextra-amino acids, glycosylation sites, cytosine for specific disulfide bridge formation, for example of possible modifications. The modified peptides can be chemically synthesized, or the isolated gene can be site-directed mutagenized, or a synthetic gene can be synthesized and expressed in bacteria, yeast, baculovirus, tissue culture and so on.

The polynucleotide encoding LipL32 includes the nucleotide sequence in FIG. 1 (SEQ ID NO:1), as well as nucleic acid sequences complementary to that sequence. When the sequence is RNA, the deoxyribonucleotides A, G, C, and T of SEQ ID NO:1 are replaced by ribonucleotides A, C, C, and U, respectively. Also included in the invention are fragments (portions) of the above-described nucleic acid sequences that are at least 15 bases in length, which is sufficient to permit the fragment to selectively hybridize to DNA that encodes the protein of FIG. 1 (e.g., SEQ ID NO:2). ASelective hybridization≅ as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes related from unrelated nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2× SSC/0.1% SDS at about room temperature (hybridization conditions); 0.2× SSC/0.1% SDS at about room temperature (low stringency conditions); 0.2× SSC/0.1% SDS at about 42EC (moderate stringency conditions); and 0.1× SSC at about 68EC (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

Specifically disclosed herein is a DNA sequence for LipL32 represented by SEQ ID NO:1. DNA sequences of the invention can be obtained by several methods. For example, the DNA can be isolated using hybridization or computer-based techniques which are well known in the art. These include, but are not limited to: 1) hybridization of genomic libraries with probes to detect homologous nucleotide sequences; 2) antibody screening of expression libraries to detect cloned DNA fragments with shared structural features; 3) polymerase chain reaction (PCR) on genomic DNA using primers capable of annealing to the DNA sequence of interest; and 4) computer searches of sequence databases for similar sequences.

In general, the primers used according to the method of the invention embrace oligonucleotides of sufficient length and appropriate sequence which provides specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acid of interest. Specifically, the term Aprimer≅ as used herein refers to a sequence comprising two or more deoxyribonucleotides or ribonucleotides, preferably at least eight, which sequence is capable of initiating synthesis of a primer extension product that is substantially complementary to a target nucleic acid strand. The oligonucleotide primer typically contains 15–22 or more nucleotides, although it may contain fewer nucleotides as long as the primer is of sufficient specificity to allow essentially only the amplification of the specifically desired target nucleotide sequence (i.e., the primer is substantially complementary).

Experimental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide compound.

Primers used according to the method of the invention are designed to be Asubstantially≅ complementary to each strand of mutant nucleotide sequence to be amplified. Substantially complementary means that the primers must be sufficiently complementary to hybridize with their respective strands under conditions which allow the agent for polymerization to function. In other words, the primers should have sufficient complementarily with the flanking sequences to hybridize therewith and permit amplification of the mutant nucleotide sequence. Preferably, the 3' terminus of the primer that is extended has perfectly base paired complementarity with the complementary flanking strand.

Oligonucleotide primers used according to the invention are employed in any amplification process that produces increased quantities of target nucleic acid. Typically, one primer is complementary to the negative (−) strand of the mutant nucleotide sequence and the other is complementary to the positive (+) strand. Annealing the primers to denatured nucleic acid followed by extension with an enzyme, such as the large fragment of DNA Polymerase I (Klenow) or Taq DNA polymerase and nucleotides or ligases, results in newly synthesized + and −strands containing the target nucleic acid. Because these newly synthesized nucleic acids are also templates, repeated cycles of denaturing, primer annealing, and extension results in exponential production of the region (i.e., the target mutant nucleotide sequence) defined by the primer. The product of the amplification reaction is a discrete nucleic acid duplex with termini corresponding to the ends of the specific primers employed. Those of skill in the art will know of other amplification methodologies which can also be utilized to increase the copy number of target nucleic acid.

The amplified product may be detected by Southern blot analysis, without using radioactive probes. In such a process, for example, a small sample of DNA containing a very low level of LipL32 nucleotide sequence is amplified, and analyzed via a Southern blotting technique. The use of non-radioactive probes or labels is facilitated by the high level of the amplified signal.

Preferably the LipL32 polynucleotide of the invention is derived from a leptospiral organism. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of DNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981).

When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned.

DNA sequences encoding LipL32 can be expressed in vitro by DNA transfer into a suitable host cell. AHost cells≅ are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the LipL32 polynucleotide sequences may be inserted into a recombinant expression vector. The term Arecombinant expression vector≅ refers to a plasmid, virus or other vehicle known in the art that has been manipulated by insertion or incorporation of the LipL32 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56: 125, 1987), the pMSXND expression vector for expression in mammalian cells (Lee and Nathans, *J. Biol. Chem.*, 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding LipL32 can be expressed in either prokaryotes or eukaryotes. Hosts can include microbial, yeast, insect and mammalian organisms. Such vectors are used to incorporate DNA sequences of the invention.

Methods which are well known to those skilled in the art can be used to construct expression vectors containing the LipL32 coding sequence and appropriate transcriptional/translational control signals. These methods include in vitro recombinant DNA techniques, synthetic techniques, and in vivo recombination/genetic techniques. (See, for example, the techniques described in Maniatis et al., 1989 Molecular Cloning A Laboratory Manual, Cold Spring Harbor Laboratory, N.Y.)

A variety of host-expression vector systems may be utilized to express the LipL32 coding sequence. These include but are not limited to microorganisms such as bacteria transformed with recombinant bacteriophage DNA, plasmid DNA or cosmid DNA expression vectors containing the LipL32 coding sequence; yeast transformed with recombinant yeast expression vectors containing the LipL32 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the LipL32 coding sequence; insect cell systems infected with recombinant virus expression vectors (e.g., baculovirus) containing the LipL32 coding sequence; or animal cell systems infected with recombinant virus expression vectors (e.g., retroviruses, adenovirus, vaccinia virus) containing the LipL32 coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see e.g., Bitter et al., *Methods in Enzymology* 153:516, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted LipL32 coding sequence.

In yeast, a number of vectors containing constitutive or inducible promoters may be used. For a review see, *Current Protocols in Molecular Biology*, Vol. 2, 1988, Ed. Ausubel et al., Greene Publish. Assoc. & Wiley Interscience, Ch. 13; Grant et al., Expression and Secretion Vectors for Yeast, in Methods in Enzymology, 153:516, 1987; Glover, 1986, *DNA Cloning*, Vol. 11, IRL Press, Wash., D.C., Ch. 3; and Bitter, Heterologous Gene Expression in Yeast, *Methods in Enzymology*, 152:673, 1987; and *The Molecular Biology of the Yeast Saccharomyces*, 1982, Eds. Strathem et al., Cold Spring Harbor Press, Vols. I and II. A constitutive yeast promoter such as ADH or LEU2 or an inducible promoter such as GAL may be used (Cloning in Yeast, Ch. 3, R. Rothstein In: *DNA Cloning Vol. 11, A Practical Approach*, Ed. DM Glover, 1986, IRL Press, Wash., D.C.). Alternatively, vectors may be used which promote integration of foreign DNA sequences into the yeast chromosome.

The genetic construct can be designed to provide additional benefits, such as, for example addition of C-terminal or N-terminal amino acid residues that would facilitate purification by trapping on columns or by use of antibodies. All those methodologies are cumulative. For example, a synthetic gene can later be mutagenized. The choice as to the method of producing a particular construct can easily be made by one skilled in the art based on practical considerations: size of the desired peptide, availability and cost of starting materials, etc. All the technologies involved are well established and well known in the art. See, for example, Ausubel et al., *Current Protocols in Molecular Biology*, Volumes 1 and 2 (1987), with supplements, and Maniatis et al., *Molecular Cloning, a Laboratory Manual*, Cold Spring Harbor Laboratory (1989). Yet other technical references are known and easily accessible to one skilled in the art.

Antibodies that Bind to LipL32

In another embodiment, the present invention provides antibodies that bind to LipL32. Such antibodies are useful for research and diagnostic tools in the study of spirochetal infection in general, and specifically the development of more effective anti-leptospiral therapeutics. Such antibodies may be administered alone or contained in a pharmaceutical composition comprising antibodies against LipL32 and other reagents effective as anti-spirochete therapeutics.

During an investigation of LipL32, the inventor found that an antibody raised to the outer membrane protein OspA of Borrelia cross-reacted to the LipL32 polypeptide (see Example 3). This finding indicates that LipL32 of Leptospira and OspA of Borrelia share a common antigenic epitope. Such an epitope may also be common to other outer membrane proteins present in additional pathogenic spirochetes. Thus, it is envisioned that antibodies of the invention can be used to detect the presence of an antigenic determinant resulting from a spirochetal-associated pathology in a subject having, or suspected of having, such a pathology.

The term Aepitope≅, as used herein, refers to an antigenic determinant on an antigen, such as a LipL32 polypeptide, to which the paratope of an antibody, such as an LipL32-specific antibody, binds. Antigenic determinants usually consist of chemically active surface groupings of molecules, such as amino acids or sugar side chains, and can have specific three-dimensional structural characteristics, as well as specific charge characteristics.

Antibodies which bind to the LipL32 polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the Aimage≅ of the epitope bound by the first monoclonal antibody.

An antibody suitable for binding to LipL32 is specific for at least one portion of an extracellular region of the LipL32 polypeptide, as shown in FIG. 1 (SEQ ID NO:2). For example, one of skill in the art can use the peptides to generate appropriate antibodies of the invention. Antibodies of the invention include polyclonal antibodies, monoclonal antibodies, and fragments of polyclonal and monoclonal antibodies.

The preparation of polyclonal antibodies is well-known to those skilled in the art. See, for example, Green et al., *Production of Polyclonal Antisera*, in *Immunochemical Protocols* (Manson, ed.), pages 1–5 (Humana Press 1992); Coligan et al., *Production of Polyclonal Antisera in Rabbits, Rats, Mice and Hamsters*, in *Current Protocols in Immunology*, section 2.4.1 (1992), which are hereby incorporated by reference.

The preparation of monoclonal antibodies likewise is conventional. See, for example, Kohler & Milstein, *Nature* 256:495 (1975); Coligan et al., sections 2.5.1–2.6.7; and Harlow et al., *Antibodies: A Laboratory Manual*, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., *Purification of Immunoglobulin G (IgG)*, in *Methods in Molecular Biology*, Vol. 10, pages 79–104 (Humana Press 1992). Methods of in vitro and in vivo multiplication of monoclonal antibodies is well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., osyngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. For example, antibodies of the present invention may also be derived from subhuman primate antibody. General techniques for raising therapeutically useful antibodies in baboons can be found, for example, in Goldenberg et al., International Patent Publication WO 91/11465 (1991) and Losman et al., *Int. J. Cancer* 46:310 (1990), which are hereby incorporated by reference.

Alternatively, a therapeutically useful anti-LipL32 antibody may be derived from a Ahumanized≡ monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989), which is hereby incorporated in its entirety by reference. Techniques for producing humanized monoclonal antibodies are described, for example, by Jones et al., *Nature* 321: 522 (1986); Riechmann et al., *Nature* 332: 323 (1988); Verhoeyen et al., *Science* 239: 1534 (1988); Carter et al., *Proc. Nat'l Acad. Sci. USA* 89: 4285 (1992); Sandhu, *Crit. Rev. Biotech.* 12: 437 (1992); and Singer et al., *J. Immunol.* 150: 2844 (1993), which are hereby incorporated by reference.

Antibodies of the invention also may be derived from human antibody fragments isolated from a combinatorial immunoglobulin library. See, for example, Barbas et al., *Methods: A Companion to Methods in Enzymology*, Vol. 2, page 119 (1991); Winter et al., *Ann. Rev. Immunol.* 12: 433 (1994), which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been Aengineered≡ to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994); Lonberg et al., Nature 368:856 (1994); and Taylor et al., *Int. Immunol.* 6:579 (1994), which are hereby incorporated by reference.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and No. 4,331,647, and references contained therein. These patents are hereby incorporated in their entireties by reference. See also Nisonhoff et al., *Arch. Biochem. Biophys.* 89:230 (1960); Porter, *Biochem. J.* 73:119 (1959); Edelman et al., *Methods in Enzymology*, Vol. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., *Proc. Nat'l Acad. Sci. USA* 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., *Methods: A Companion to Methods in Enzymology*, Vol. 2, page 97 (1991); Bird et al., *Science* 242:423–426 (1988); Ladner et al., U.S. Pat. No. 4,946,778; Pack et al., *Bio/Technology* 11: 1271–77 (1993); and Sandhu, supra.

Another form of an antibody fragment is a peptide coding for a single complementarity determining region (CDR). CDR peptides (Aminimal recognition units≅) can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology*, Vol. 2, page 106 (1991).

When used for immunotherapy, the monoclonal antibodies of the invention that binds to LipL32 may be unlabeled or labeled with a therapeutic agent. These agents can be coupled either directly or indirectly to the monoclonal antibodies of the invention. One example of indirect coupling is by use of a spacer moiety. These spacer moieties, in turn, can be either insoluble or soluble (Diener, et al., *Science*, 231:148, 1986) and can be selected to enable drug release from the monoclonal antibody molecule at the target site. Examples of therapeutic agents which can be coupled to the monoclonal antibodies of the invention for immunotherapy are drugs, radioisotopes, lectins, and toxins.

The labeled or unlabeled monoclonal antibodies of the invention can also be used in combination with therapeutic agents such as those described above. Especially preferred are therapeutic combinations comprising the monoclonal antibody of the invention and immunomodulators and other biological response modifiers.

When the monoclonal antibody of the invention is used in combination with various therapeutic agents, such as those described herein, the administration of the monoclonal antibody and the therapeutic agent usually occurs substantially contemporaneously. The term Asubstantially contemporaneously≅ means that the monoclonal antibody and the therapeutic agent are administered reasonably close together with respect to time. Usually, it is preferred to administer the therapeutic agent before the monoclonal antibody. For example, the therapeutic agent can be administered 1 to 6 days before the monoclonal antibody. The administration of the therapeutic agent can be daily, or at any other interval, depending upon such factors, for example, as the nature of the disorder, the condition of the patient and half-life of the agent.

The dosage ranges for the administration of monoclonal antibodies of the invention are those large enough to produce the desired effect in which the onset symptoms of the leptospiral disease are ameliorated. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when the monoclonal antibodies of the invention are administered conjugated with therapeutic agents, lower dosages, comparable to those used for in vivo diagnostic imaging, can be used.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

Pharmaceutical Compositions for Preventing or Treating a Spirochetal-associated Pathology Since antibodies raised to OspA of *Borrelia burgdorferi* cross-react with the LipL32 polypeptide of the invention, a common epitope is likely to be present on both polypeptides. This finding suggests that spirochetal outer membrane proteins may share common antigenic determinants which can be used to immunize a subject against multiple spirochete-associated disease states. For example, challenging a subject with the LipL32 polypeptide (SEQ ID NO:2) may confer protective immunity to other spirochetal disease states, such as Lyme disease, as well as immunity to leptospirosis.

It is envisioned that methods of the present invention can be used to treat spirochetal-associated disease states or, more specifically, Leptospira-associated disease states. Generally, the terms Atreating,≅ Atreatment,≅ and the like are used herein to mean obtaining a desired pharmacologic and/or physiologic effect. The effect may be prophylactic in terms of completely or partially preventing a spirochete infection or disease (e.g., leptospirosis or Lyme disease) or sign or symptom thereof, and/or may be therapeutic in terms of a partial or complete cure for an infection or disease and/or adverse effect attributable to the infection or disease. ATreating≅ as used herein covers any treatment of (e.g., complete or partial), or prevention of, an infection or disease in a mammal, particularly a human, and includes:

(a) preventing the disease from occurring in a subject that may be predisposed to the disease, but has not yet been diagnosed as having it;

(b) inhibiting the infection or disease, i.e., arresting its development; or (c) relieving or ameliorating the infection or disease, i.e., cause regression of the infection or disease.

Thus, the invention includes various pharmaceutical compositions useful for ameliorating symptoms attributable to a spirochete infection or, alternatively, for inducing a protective immune response to prevent such an infection. The pharmaceutical compositions according to the invention are prepared by bringing an antibody against LipL32, a peptide or peptide derivative of LipL32, a LipL32 mimetic, or a LipL32-binding agent according to the present invention into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in *Remington's Pharmaceutical Sciences*, 15th ed. Easton: Mack Publishing Co., 1405–1412, 1461–1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's *The Pharmacological Basisfor Therapeutics* (7th ed.).

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically. By Atherapeutically effective dose≅ is meant the quantity of a compound according to the invention necessary to prevent, to cure or at least partially arrest the symptoms of the disease and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Langer, *Science*, 249: 1527, (1990); Gilman et al. (eds.) (1990), each of which is herein incorporated by reference.

In one embodiment, the invention provides a pharmaceutical composition useful for inducing an immune response to a virulent spirochete in an animal comprising an immunologically effective amount of LipL32 in a pharmaceutically acceptable carrier. AAdministering≅ the pharmaceutical composition of the present invention may be accomplished by any means known to the skilled artisan. By Asubject≅ is meant any mammal, preferably a human. The term Aimmunogenically effective amount,≅ as used in describing the invention, is meant to denote that amount of Leptospira antigen which is necessary to induce, in an animal, the production of a protective immune response to Leptospira or any other pathogenic spirochete. The LipL32 protein of the invention is particularly useful in sensitizing the immune system of an animal such that, as one result, an immune response is produced which ameliorates the effect of a spirochetal infection.

The LipL32 protein can be administered parenterally by injection, rapid infusion, nasopharyngeal absorption, dermal absorption, and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners and elixirs containing inert diluents commonly used in the art, such as purified water.

In addition to the inert diluents, such compositions can also include adjuvants, wetting agents, and emulsifying and suspending agents. Adjuvants are substances that can be used to nonspecifically augment a specific immune response. Normally, the adjuvant and the antigen are mixed prior to presentation to the immune system, or presented separately, but into the same site of the animal being immunized. Adjuvants can be loosely divided into several groups based on their composition. These groups include oil adjuvants (for example, Freund's Complete and Incomplete), mineral salts (for example, $AlK(SO_4)_2$, $AlNa(SO_4)_2$, $AlNH_4(SO_4)$, silica, alum, $Al(OH)_3$, $Ca_3(PO_4)_2$, kaolin, and carbon), polynucleotides (for example, poly IC and poly AU acids), and certain natural substances (for example, wax D from Mycobacterium tuberculosis, as well as substances found in *Corynebacterium parvum, Bordetella pertussis*, and members of the genus Brucella).

The method of the invention also includes slow release antigen delivery systems such as microencapsulation of antigens into liposomes. Such systems have been used as an approach to enhance the immunogenicity of proteins without the use of traditional adjuvants. Liposomes in the blood stream are generally taken up by the liver and spleen, and are easily phagocytosed by macrophages. Liposomes also allow co-entrapment of immunomodulatory molecules along with the antigens, so that such molecules may be delivered to the site of antigen encounter, allowing modulation of the immune system towards protective responses.

Many different techniques exist for the timing of the immunizations when a multiple immunization regimen is utilized. It is possible to use the antigenic preparation of the invention more than once to increase the levels and diversity of expression of the immune response of the immunized animal. Typically, if multiple immunizations are given, they will be spaced two to four weeks apart. Subjects in which an immune response to Leptospira is desirable include humans, dogs, cattle, horses, deer, mice, goats, wolves and sheep.

Generally, the dosage of LipL32 protein administered to a subject will vary depending on such factors as age, condition, sex and extent of disease, if any, and other variables which can be adjusted by one of ordinary skill in the art.

In another embodiment, the invention provides a method for identifying a compound which binds to LipL32. The method includes incubating components comprising the compound and LipL32 under conditions sufficient to allow the components to interact and measuring the binding of the compound to LipL32. Compounds that bind to LipL32 include peptides, peptidomimetics, polypeptides, chemical compounds and biologic agents as described above.

Incubating includes conditions which allow contact between the test compound and LipL32. Contacting includes in solution and in solid phase. The test ligand(s)/compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

In addition to generating antibodies which bind to antigenic epitopes of LipL32, it is further envisioned that the method of the invention can be used to induce cellular responses, particularly cytotoxic T-lymphocytes (CTLs), to antigenic epitopes of LipL32. Typically, unmodified soluble proteins fail to prime major histocompatibility complex (MHC) class I-restricted CTL responses whereas particulate proteins are extremely immunogenic and have been shown to prime CTL responses in vivo. CTL epitopes and helper epitopes have been identified in proteins from many infectious pathogens. Further, these epitopes can be produced concurrently such that multiple epitopes can be delivered in a form that can prime MHC class I restricted CTL responses. An example of a system that can produce recombinant protein particles carrying one or more epitopes entails the use of the p1 protein of the retrotransposon Ty1 of *Saccharomyces cerevisiae* (Adams, et al., *Nature*, 329:68, 1987). Sequences encoding CTL epitopes can, for example, be fused to the C-terminus of p1 and the resulting Ty virus-like particles (Ty-VLPs) may be able to generate a CTL response. Thus, conserved regions of spirochetal antigens can be identified and incorporated together in a particle which enables the host immune system to mount an effective immune response against multiple spirochetal organisms. Further, the method of the invention can be used to generate particles with multiple epitopes to a single protein, such as LipL32, or multiple epitopes from various spirochetal proteins.

Also included in the screening method of the invention are combinatorial chemistry methods for identifying chemical compounds that bind to LipL32. See, for example, Plunkett and Ellman, A*Combinatorial Chemistry and New Drugs*≡, *Scientific American*, April, p.69, (1997).

Detection of LipL32 In vivo and In vitro

In a further embodiment, the invention provides a method of detecting a Leptospira-associated disorder in a subject comprising contacting a cell component containing LipL32 with a reagent which binds to the cell component. The cell component can be nucleic acid, such as DNA or RNA, or it can be protein. When the component is nucleic acid, the reagent is a nucleic acid probe or PCR primer. When the cell component is protein, the reagent is an antibody probe. The probes are detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

For purposes of the invention, an antibody or nucleic acid probe specific for LipL32 may be used to detect the presence of LipL32 polypeptide (using antibody) or polynucleotide (using nucleic acid probe) in biological fluids or tissues. Any specimen containing a detectable amount of LipL32 antigen or polynucleotide can be used. A preferred specimen of this invention is blood, urine, cerebrospinal fluid, synovial fluid or tissue of endothelial origin.

Another technique which may also result in greater sensitivity consists of coupling antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific antihapten antibodies.

Alternatively, LipL32 polypeptide can be used to detect antibodies to LipL32 polypeptide in a specimen. The LipL32 of the invention is particularly suited for use in immunoassays in which it can be utilized in liquid phase or bound to a solid phase carrier. In addition, LipL32 used in these assays can be detectably labeled in various ways.

Examples of immunoassays which can utilize the LipL32 of the invention are competitive and noncompetitive immunoassays in either a direct or indirect format. Examples of such immunoassays are the radioimmunoassay (RIA), the sandwich (immunometric assay) and the Western blot assay. Detection of antibodies which bind to the LipL32 of the invention can be done utilizing immunoassays which run in either the forward, reverse, or simultaneous modes, including immunohistochemical assays on physiological samples. The concentration of LipL32 which is used will vary depending on the type of immunoassay and nature of the detectable label which is used. However, regardless of the type of immunoassay which is used, the concentration of LipL32 utilized can be readily determined by one of ordinary skill in the art using routine experimentation.

The LipL32 of the invention can be bound to many different carriers and used to detect the presence of antibody specifically reactive with the polypeptide. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding LipL32 or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

For purposes of the invention, the antibody which binds to LipL32 of the invention may be present in various biological fluids and tissues. Any sample containing a detectable amount of antibodies to LipL32 can be used. Typically, a sample is a liquid such as urine, saliva, cerebrospinal fluid, blood, serum and the like, or a solid or semi-solid such as tissue, feces and the like. Preferably, the sample is serum from the patient.

The monoclonal antibodies of the invention, directed toward LipL32, are also useful for the in vivo detection of antigen. The detectably labeled monoclonal antibody is given in a dose which is diagnostically effective. The term Adiagnostically effective≡ means that the amount of detectably labeled monoclonal antibody is administered in sufficient quantity to enable detection of Leptospira LipL32 antigen for which the monoclonal antibodies are specific.

The concentration of detectably labeled monoclonal antibody which is administered should be sufficient such that the binding to those cells, body fluid, or tissue having LipL32 is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the subject. Such dosages may vary, for example, depending on whether multiple injections are given, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 key range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used to monitor the course of amelioration of Leptospira-associated disorder. Thus, by measuring the increase or decrease of Leptospira LipL32 polypeptide or antibodies to LipL32 polypeptide present in various body fluids or tissues, it would be possible to determine whether a particular therapeutic regiment aimed at ameliorating the disorder is effective.

In another embodiment, nucleic acid probes can be used to identify LipL32 nucleic acid from a specimen obtained from a subject suspected of containing a pathogenic Leptospira. Examples of specimens from which nucleic acid sequence encoding LipL32 can be derived because of leptospiral infection include human, swine, porcine, feline, canine, equine, murine, cervine, caprine, lupine, leporidine and bovine species. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.* 9:879, 1981).

In an embodiment of the invention, purified nucleic acid fragments containing intervening sequences or oligonucleotide sequences of 10–50 base pairs are radioactively labeled. The labeled preparations are used to probe nucleic acid from a specimen by the Southern hybridization technique. Nucleotide fragments from a specimen, before or after amplification, are separated into fragments of different molecular masses by gel electrophoresis and transferred to filters that bind nucleic acid. After exposure to the labeled probe, which will hybridize to nucleotide fragments containing target nucleic acid sequences, binding of the radioactive probe to target nucleic acid fragments is identified by autoradiography (see *Genetic Engineering*, 1, ed. Robert Williamson, Academic Press, (1981), 72–81). Alternatively, nucleic acid from the specimen can be bound directly to filters to which the radioactive probe selectively attaches by binding nucleic acids having the sequence of interest. Specific sequences and the degree of binding is quantitated by directly counting the radioactive emissions.

Where the target nucleic acid is not amplified, detection using an appropriate hybridization probe may be performed directly on the separated nucleic acid. In those instances where the target nucleic acid is amplified, detection with the appropriate hybridization probe would be performed after amplification.

The probes of the present invention can be used for examining the distribution of the specific fragments detected, as well as the quantitative (relative) degree of binding of the probe for determining the occurrence of specific strongly binding (hybridizing) sequences, thus indicating the likelihood for an subject having or predisposed to having increased muscle mass.

For the most part, the probe will be detectably labeled with an atom or inorganic radical, most commonly using radionuclides, but also heavy metals can be used. Conveniently, a radioactive label may be employed. Radioactive labels include $^{32}$P, $^{125}$I, $^{3}$H, $^{14}$C, $^{111}$In, $^{99m}$Tc, or the like. Any radioactive label may be employed which provides for an adequate signal and has sufficient half-life. Other labels include ligands, which can serve as a specific binding pair member for a labeled ligand, and the like. A wide variety of labels routinely employed in immunoassays can readily be employed in the present assay. The choice of the label will be governed by the effect of the label on the rate of hybridization and binding of the probe to mutant nucleotide sequence. It will be necessary that the label provide sufficient sensitivity to detect the amount of mutant nucleotide sequence available for hybridization. Other considerations will be ease of synthesis of the probe, readily available instrumentation, ability to automate, convenience, and the like.

The manner in which the label is bound to the probe will vary depending upon the nature of the label. For a radioactive label, a wide variety of techniques can be employed. Commonly employed is nick translation with an a 32P-DNTP or terminal phosphate hydrolysis with alkaline phosphatase followed by labeling with radioactive $^{32}$P employing $^{32}$P-NTP and T4 polynucleotide kinase. Alternatively, nucleotides can be synthesized where one or more of the elements present are replaced with a radioactive isotope, e.g., hydrogen with tritium. If desired, complementary labeled strands can be used as probes to enhance the concentration of hybridized label.

Where other radionucleotide labels are involved, various linking groups can be employed. A terminal hydroxyl can be esterified, with inorganic acids, e.g., $^{32}P$ phosphate, or $^{14}C$ organic acids, or else esterified to provide linking groups to the label. Alternatively, intermediate bases may be substituted with activatable linking groups that can then be linked to a label.

Enzymes of interest as reporter groups will primarily be hydrolases, particularly esterases and glycosidases, or oxidoreductases, particularly peroxidases. Fluorescent compounds include fluorescein and its derivatives, rhodamine and its derivatives, dansyl, umbelliferone, and so forth. Chemiluminescers include luciferin, and 2,3-dihydrophthalazinediones (e.g., luminol).

The probe can be employed for hybridizing to a nucleotide sequence affixed to a water insoluble porous support. Depending upon the source of the nucleic acid, the manner in which the nucleic acid is affixed to the support may vary. Those of ordinary skill in the art know, or can easily ascertain, different supports that can be used in the method of the invention.

The nucleic acid from a specimen can be cloned and then spotted or spread onto a filter to provide a plurality of individual portions (plaques). The filter is an inert porous solid support, e.g., nitrocellulose. Any cells (or phage) present in the specimen are treated to liberate their nucleic acid. The lysing and denaturation of nucleic acid, as well as the subsequent washings, can be achieved with an appropriate solution for a sufficient time to lyse the cells and denature the nucleic acid. For lysing, chemical lysing will conveniently be employed, as described previously for the lysis buffer. Other denaturation agents include elevated temperatures, organic reagents, e.g., alcohols, amides, amines, ureas, phenols and sulfoxides or certain inorganic ions, e.g., thiocyanate and perchlorate.

After denaturation, the filter is washed in an aqueous buffered solution, such as Tris, generally at a pH of about 6 to 8, usually 7. One or more washings may be involved, conveniently using the same procedure as employed for the lysing and denaturation. After the lysing, denaturing, and washes have been accomplished, the nucleic acid spotted filter is dried at an elevated temperature, generally from about 50EC to 70EC. Under this procedure, the nucleic acid is fixed in position and can be assayed with the probe when convenient.

Pre-hybridization may be accomplished by incubating the filter with the hybridization solution without the probe at a mildly elevated temperature for a sufficient time to thoroughly wet the filter. Various hybridization solutions may be employed, comprising from about 20% to 60% volume, preferably 30%, of an inert polar organic solvent. A common hybridization solution employs about 50% formamide, about 0.5 to 1M sodium chloride, about 0.05 to 0.1M sodium citrate, about 0.05 to 0.2% sodium dodecylsulfate, and minor amounts of EDTA, ficoll (about 300–500 kD), polyvinylpyrrolidone, (about 250–500 kD) and serum albumin. Also included in the hybridization solution will generally be from about 0.5 to 5 mg/ml of sonicated denatured DNA, e.g., calf thymus of salmon sperm; and optionally from about 0.5 to 2% wt/vol glycine. Other additives may also be included, such as dextran sulfate of from about 100 to 1,000 kD and in an amount of from about 8 to 15 weight percent of the hybridization solution.

The particular hybridization technique is not essential to the invention. Other hybridization techniques are described by Gall and Pardue, (*Proc. Natl. Acad. Sci.* 63:378, 1969); and John, et al., (*Nature*, 223:582, 1969). As improvements are made in hybridization techniques they can readily be applied in the method of the invention.

The amount of labeled probe present in the hybridization solution will vary widely, depending upon the nature of the label, the amount of the labeled probe that can reasonably bind to the filter, and the stringency of the hybridization. Generally, substantial excess over stoichiometric concentrations of the probe will be employed to enhance the rate of binding of the probe to the fixed target nucleic acid.

In nucleic acid hybridization reactions, the conditions used to achieve a particular level of stringency will vary, depending on the nature of the nucleic acids being hybridized. For example, the length, degree of complementarity, nucleotide sequence compound (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2× SSC/0.1% SDS at about room temperature (hybridization conditions); 0.2× SSC/0.1% SDS at about room temperature (low stringency conditions); 0.2× SSC/0.1% SDS at about 42EC (moderate stringency conditions); and 0.1× SSC at about 68EC (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

After the filter has been contacted with a hybridization solution at a moderate temperature for a period of time sufficient to allow hybridization to occur, the filter is then introduced into a second solution having analogous concentrations of sodium chloride, sodium citrate and sodium dodecylsulfate as provided in the hybridization solution. The time the filter is maintained in the second solution may vary from five minutes to three hours or more. The second solution determines the stringency, dissolving cross duplexes and short complementary sequences. After rinsing the filter at room temperature with dilute sodium citrate-sodium chloride solution, the filter may now be assayed for the presence of duplexes in accordance with the nature of the label. Where the label is radioactive, the filter is dried and exposed to X-ray film.

The label may also comprise a fluorescent moiety that can then be probed with a specific fluorescent antibody. Horseradish peroxidase enzyme can be conjugated to the antibody to catalyze a chemiluminescent reaction. Production of light can then be seen on rapid exposure to film.

Kits for Detection of LipL32

The materials for use in the method of the invention are ideally suited for the preparation of a kit. Such a kit may comprise a carrier means being compartmentalized to receive one or more container means such as vials, tubes, and the like, each of the container means comprising one of the separate elements to be used in the method. For example, one of the container means may comprise a LipL32 binding reagent, such as an antibody or nucleic acid. A second container may further comprise LipL32 polypeptide. The constituents may be present in liquid or lyophilized form, as desired.

One of the container means may comprise a probe which is or can be detectably labeled. Such probe may be an antibody or nucleotide specific for a target protein, or fragments thereof, or a target nucleic acid, or fragment thereof, respectively, wherein the target is indicative, or correlates with, the presence of LipL32. For example, oligonucleotide probes of the present invention can be included in a kit and used for examining the presence of LipL32 nucleic acid, as well as the quantitative (relative) degree of binding of the probe for determining the occurrence of specific strongly binding (hybridizing) sequences, thus indicating the likelihood for an subject having a Leptospira-associated pathology.

The kit may also contain a container comprising a reporter-means, such as a biotin-binding protein, such as avidin or streptavidin, bound to a reporter molecule, such as an enzymatic, fluorescent, or radionucleotide label to identify the detectably labeled oligonucleotide probe.

Where the kit utilizes nucleic acid hybridization to detect the target nucleic acid, the kit may also have containers containing nucleotide(s) for amplification of the target nucleic acid sequence. When it is desirable to amplify the target nucleic acid sequence, such as a LipL32 nucleic acid sequence, this can be accomplished using oligonucleotide(s) that are primers for amplification. These oligonucleotide primers are based upon identification of the flanking regions contiguous with the target nucleotide sequence.

The kit may also include a container containing antibodies which bind to a target protein, or fragments thereof. Thus, it is envisioned that antibodies which bind to LipL32, or fragments thereof, can be included in a kit.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLE 1

Method for Determining the Amino Acid Sequence of LipL32

A 20 kD proteolytic fragment of LipL32 was sequenced by the following method: L. kirschneri cells ($4 \times 10^{11}$) were washed two times in PBS and resuspended in 30 ml of ice cold TENP buffer (50 mM Tris pH 8, 1 mM EDTA, 100 mM NaCl, 0.1 mM PMSF). The cells were disrupted by tip sonication. The membrane fraction was recovered by centrifugation for 20 minutes at 12,000× g, and washed once in TENP buffer. The membrane proteins were separated on a 12.5% SDS-PAGE gel. A test strip was stained with Coomassie brilliant blue in order to locate the 32 kD band, which was cut out of the remainder of the gel and loaded onto a second SDS-PAGE gel in the presence of staphylococcal V8 protease at a concentration of 100 mg ml$^{-1}$ (Sigma). The proteins were allowed to migrate into the stacking gel by electrophoresis, the current was disconnected for 45 min, and then electrophoresis was completed. The polypeptide fragments were transferred to Trans-Blot polyvinylidene difluoride protein-sequencing membrane (Bio-Rad, Richmond, Calif.) and submitted to the UCLA Protein Microsequencing Facility. N-terminal amino acid sequence analysis was performed on Jun. 17, 1996 on a Porton 1090-E gas phase sequenator with on-line detection of PTH amino acids. Two partial amino acid sequences were obtained from sequencing LipL32 peptides: AFKAATPEEKSMD(H)VQD (SEQ ID NO:5) and RHNKYNSLTRIKIPNP(P)KSFDDLKNIDTKKL(L) (SEQ ID NO:6)

EXAMPLE 2

Isolation and Characterization of the LipL32 Gene

Two oligonucleotides were designed based upon two independent regions of the LipL32 sequence: RHNKYNSLTRIKIPNP(P)KSFDDLKNIDTKKL(L) (SEQ ID NO:6)

```
                    32A-1                    32A-2
Oligonucleotide 32A-1:  GDCAYAAYAARTAYAAYWSYYT    (SEQ ID NO:3)
Oligonucleotide 32A-2:  AARAAYATHGAYACNAARAARYT   (SEQ ID NO:4)
```

In the above oligonucleotide sequences D represents A or G or T/U, Y represents C or T/U, R represents A or G, W represents A or T/U, S represents C or G, H represents A or C or T/U and N represents A or C or G or T/U.

Oligonucleotide 32A-1 and the anti-parallel of Oligonucleotide 32A-2 were used to PCR amplify the intervening region of the lipL32 gene. The resulting 90 bp amplification product was sequenced from both ends and used in hybridization studies.

Southern hybridization studies using this LipL32 PCR product as a probe revealed binding to a single 5 kb band in digests of total genomic L. kirschneri serovar grippotyphosa, strain RM52 DNA treated with the restriction enzyme EcoRI. The lipL32 gene was cloned from a Lambda Zap II library of L. kirschneri EcoRI DNA fragments. Analysis of the lipL32 sequence indicates that it encodes a membrane lipoprotein with a nineteen amino acid signal peptide, a lipoprotein signal peptidase cleavage site, and an amino-terminal cysteine. The mature protein would be 253 amino acids long, with a predicted molecular weight of 27.6 kD.

EXAMPLE 3

Recognition of LipL32 Polypeptide by Antibodies that Bind to Borrelia OspA

Leptospira kirschneri serovar grippotyphosa whole organisms were solubilized in final sample buffer composed of 62.5 mM Tris hydrochloride (pH 6.8), 10% glycerol, 5% 2-mercaptoethanol, and 2% sodium dodecyl sulfate. Proteins were separated by sodium dodecyl sulfate-polyacrylamide gel electrophoresis on a 12% gel with a discontinuous buffer system and transferred to nitrocellulose filters (Schleicher and Schuell) for immunoblotting. The nitrocellulose filter was blocked with 5% nonfat dry milk in PBS (0.1 M phosphate buffered saline, pH 7.4)-0.1% Tween 20 (BS-T), incubated for 1 hour with rabbit anti-OspA antiserum, and probed with donkey anti-rabbit antiserum conjugated to horseradish peroxidase (Amersham). Antigen-antibody binding was detected with enhanced chemiluminescence system (ECL; Amersham). Blots were incubated in ECL reagents for 1 minute and then exposed to XAR-5 film (Kodak). A single band was identified with an apparent molecular mass of 32-kD at the same location as the LipL32 protein.

It will be apparent to those skilled in the art that various modifications and variations can be made to the compounds and processes of this invention. Thus, it is intended that the present invention cover such modifications and variations, provided they come within the scope of the appended claims and their equivalents. Accordingly, the invention is limited only by the following claims.

What is claimed:

1. A purified LipL32 polypeptide having an amino acid sequence as set forth in SEQ ID NO:2, or peptide thereof comprising amino acid residues 20 to 272 of SEQ ID NO:2.

2. An immunogenic composition useful for inducing an immune response to a pathogenic spirochete in a subject, comprising an immunogenically effective amount of a LipL32 polypeptide comprising SEQ ID NO:2, or peptide thereof comprising amino acid residues 20 to 272 of SEQ ID NO:2, and a pharmaceutically acceptable carrier.

3. The immunogenic composition of claim 2, wherein the pharmaceutically acceptable carrier further comprises an adjuvant.

4. The immunogenic composition of claim 2, wherein the pharmaceutically acceptable carrier is a solution, suspension, or emulsion.

5. The immunogenic composition of claim 2, wherein the pathogenic spirochete is Treponema, Borrelia or Leptospira.

6. The immunogenic composition of claim 2, wherein the pathogenic spirochete is Treponema, Borrelia or Leptospira.

7. The immunogenic composition of claim 2, wherein the pathogenic spirochete is Borrelia.

8. The immunogenic composition of claim 7, wherein the pharmaceutically acceptable carrier is a solution.

* * * * *

```
                            SEQUENCE LISTING

<160> NUMBER OF SEQ ID NOS: 6

<210> SEQ ID NO 1
<211> LENGTH: 819
<212> TYPE: DNA
<213> ORGANISM: Leptospira kirschneri
<220> FEATURE:
<221> NAME/KEY: CDS
<222> LOCATION: (0)...(816)

<400> SEQUENCE:

```
gtg agc ccg ctg atc cac tca aat cct gaa gaa ttg caa aaa caa gct      768
Val Ser Pro Leu Ile His Ser Asn Pro Glu Glu Leu Gln Lys Gln Ala
                245                 250                 255 atc gct gct gaa gag tct ttg aaa aaa gct gct tct gac gcg act aag      816
Ile Ala Ala Glu Glu Ser Leu Lys Lys Ala Ala Ser Asp Ala Thr Lys
            260                 265                 270 taa                                                                   819

<210> SEQ ID NO 2
<211> LENGTH: 272
<212> TYPE: PRT
<213> ORGANISM: Leptospira kirschneri

<400> SEQUENCE: 2

Met Lys Lys Leu Ser Ile Leu Ala Ile Ser Val Ala Leu Phe Ala Ser
 1               5                  10                  15

Ile Thr Ala Cys Gly Ala Phe Gly Gly Leu Pro Ser Leu Lys Ser Ser
             20                  25                  30

Phe Val Leu Ser Glu Asp Thr Ile Pro Gly Thr Asn Glu Thr Val Lys
         35                  40                  45

Thr Leu Leu Pro Tyr Gly Ser Val Ile Asn Tyr Tyr Gly Tyr Val Lys
     50                  55                  60

Pro Gly Gln Ala Pro Asp Gly Leu Val Asp Gly Asn Lys Lys Ala Tyr
 65                  70                  75                  80

Tyr Leu Tyr Val Trp Ile Pro Ala Val Ile Ala Glu Met Gly Val Arg
                 85                  90                  95

Met Ile Ser Pro Thr Gly Glu Ile Gly Glu Pro Gly Asp Gly Asp Leu
            100                 105                 110

Val Ser Asp Ala Phe Lys Ala Ala Thr Pro Glu Glu Lys Ser Met Pro
        115                 120                 125

His Trp Phe Asp Thr Trp Ile Arg Val Glu Arg Met Ser Ala Ile Met
    130                 135                 140

Pro Asp Gln Ile Ala Lys Ala Ala Lys Ala Lys Pro Val Gln Lys Leu
145                 150                 155                 160

Asp Asp Asp Asp Gly Asp Asp Thr Tyr Lys Glu Glu Arg His Asn
                165                 170                 175

Lys Tyr Asn Ser Leu Thr Arg Ile Lys Ile Pro Asn Pro Pro Lys Ser
            180                 185                 190

Phe Asp Asp Leu Lys Asn Ile Asp Thr Lys Lys Leu Leu Val Arg Gly
        195                 200                 205

Leu Tyr Arg Ile Ser Phe Pro Thr Tyr Lys Pro Gly Glu Val Lys Gly
    210                 215                 220

Ser Phe Val Ala Ser Val Gly Leu Leu Phe Pro Pro Gly Ile Pro Gly
225                 230                 235                 240

Val Ser Pro Leu Ile His Ser Asn Pro Glu Glu Leu Gln Lys Gln Ala
                245                 250                 255

Ile Ala Ala Glu Glu Ser Leu Lys Lys Ala Ala Ser Asp Ala Thr Lys
            260                 265                 270

<210> SEQ ID NO 3
<211> LENGTH: 22
<212> TYPE: DNA
<213> ORGANISM: Artificial Sequence
<220> FEATURE:
<221> NAME/KEY: misc_feature
<222> LOCATION: (0)...(0)
<223> OTHER INFORMATION: d = A, G, or T; not C
<221> NAME/KEY: misc_feature
```

```
<222> LOCATION: (0)...(0)
<223> OTHER INFORMATION: y = T or C
<221> NAME/KEY: misc_feature
<222> LOCATION: (0)...(0)
<223> OTHER INFORMATION: r = G or A
<221> NAME/KEY: misc_feature
<222> LOCATION: (0)...(0)
<223> OTHER INFORMATION: w = A or T
<221> NAME/KEY: misc_feature
<222> LOCATION: (0)...(0)
<223> OTHER INFORMATION: s = G or C
<223> OTHER INFORMATION: Oligonucleotides for PCR

<400> SEQUENCE: 3
gdcayaayaa rtayaaywsy yt                                                    22

<210> SEQ ID NO 4
<211> LENGTH: 23
<212> TYPE: DNA
<213> ORGANISM: Artificial Sequence
<220> FEATURE:
<221> NAME/KEY: misc_feature
<222> LOCATION: (0)...(0)
<223> OTHER INFORMATION: r = A or G
<221> NAME/KEY: misc_feature
<222> LOCATION: (0)...(0)
<223> OTHER INFORMATION: y = T or C
<221> NAME/KEY: misc_feature
<222> LOCATION: (0)...(0)
<223> OTHER INFORMATION: h = A, C, or T; not G
<221> NAME/KEY: misc_feature
<222> LOCATION: (0)...(0)
<223> OTHER INFORMATION: n = A, T, G, or C
<223> OTHER INFORMATION: Oligonucleotides for PCR

<400> SEQUENCE: 4
aaraayathg ayacnaaraa ryt                                                   23

<210> SEQ ID NO 5
<211> LENGTH: 17
<212> TYPE: PRT
<213> ORGANISM: Leptospira kirschneri

<400> SEQUENCE: 5

Ala Phe Lys Ala Ala Thr Pro Glu Glu Lys Ser Met Asp His Val Gln
 1               5                  10                  15

Asp

<210> SEQ ID NO 6
<211> LENGTH: 32
<212> TYPE: PRT
<213> ORGANISM: Leptospira kirschneri

<400> SEQUENCE: 6

Arg His Asn Lys Tyr Asn Ser Leu Thr Arg Ile Lys Ile Pro Asn Pro
 1               5                  10                  15

Pro Lys Ser Phe Asp Asp Leu Lys Asn Ile Asp Thr Lys Lys Leu Leu
                20                  25                  30
```